US008034011B2

(12) United States Patent
Shaffer et al.

(10) Patent No.: US 8,034,011 B2

(45) Date of Patent: Oct. 11, 2011

(54) THORACIC STABILIZER

(75) Inventors: Thomas H. Shaffer, Chadds Ford, PA (US); Marla R. Wolfson, Wyndmoor, PA (US)

(73) Assignee: Temple University—Of The Commonwealth System of Higher Education, Philadelphia, PA (US)

(*) Notice: Subject to any disclaimer, the term of this patent is extended or adjusted under 35 U.S.C. 154(b) by 855 days.

(21) Appl. No.: 12/083,253

(22) PCT Filed: Oct. 18, 2006

(86) PCT No.: PCT/US2006/040881

§ 371 (c)(1), (2), (4) Date: Apr. 8, 2008

(87) PCT Pub. No.: WO2007/050424

PCT Pub. Date: May 3, 2007

(65) Prior Publication Data

US 2009/0020129 A1 Jan. 22, 2009

Related U.S. Application Data

(60) Provisional application No. 60/730,723, filed on Oct. 27, 2005.

(51) Int. Cl.

| | |
|---|---|
| ***A61F 5/00*** | (2006.01) |
| ***A61F 5/24*** | (2006.01) |
| ***A61F 5/28*** | (2006.01) |
| ***A61B 5/103*** | (2006.01) |
| ***A61B 5/117*** | (2006.01) |
| ***A47C 20/00*** | (2006.01) |

(52) U.S. Cl. ................................ 602/19; 5/630; 600/587

(58) Field of Classification Search ................. 128/95.1, 128/99.1, 103.1; 600/587; 602/15, 19; 5/600, 5/613, 617, 630

See application file for complete search history.

(56) References Cited

U.S. PATENT DOCUMENTS 5,484,393 A * 1/1996 McCoy ............................ 602/6

(Continued)

FOREIGN PATENT DOCUMENTS

WO WO 97/18789 5/1997

OTHER PUBLICATIONS

"Respiratory Distress Syndrome of the Newborn—Principles in Treatment" by M.A. Warley and Douglas Gairdner, Archives of Disease in Childhood, vol. 37, pp. 455-465, 1962.

(Continued)

*Primary Examiner* — Max Hindenburg
*Assistant Examiner* — Jonathan M Foreman
(74) *Attorney, Agent, or Firm* — Drinker Biddle & Reath LLP

(57) ABSTRACT

A thoracic stabilizer for limiting anterior chest wall collapse includes a platform supporting a patient and a pair of lateral supports contacting opposite sides of the patient's chest wall and applying force to limit collapse of the chest wall. The force applied by the lateral supports is varied depending on the force applied to the platform by the patient. The stabilizer includes a retractometer measuring the collapse of the chest wall. According to one embodiment, the stabilizer includes a controller that varies the force applied to the chest wall in closed-loop fashion based on the chest wall collapse measured by the retractometer using an algorithm of the controller. According to one embodiment, the stabilizer includes motors moving the lateral supports. According to another embodiment, the stabilizer includes a hydraulic system and the lateral supports include expandable fluid-filled members.

16 Claims, 4 Drawing Sheets

U.S. PATENT DOCUMENTS

| | | | | |
|---|---|---|---|---|
| 5,575,027 | A | 11/1996 | Mueller | 5/621 |
| 5,820,572 | A | 10/1998 | Palmer | 601/41 |
| 6,059,742 | A | 5/2000 | Palmer et al. | 601/41 |
| 6,533,739 | B1 | 3/2003 | Palmer et al. | 601/41 |
| 7,735,171 | B2 * | 6/2010 | Kan | 5/732 |
| 2003/0100850 | A1 | 5/2003 | Palmer et al. | 601/41 |
| 2003/0167569 | A1 * | 9/2003 | Newkirk et al. | 5/613 |
| 2004/0116840 | A1 | 6/2004 | Cantrell et al. | 601/44 |
| 2004/0162587 | A1 | 8/2004 | Hampton et al. | 607/5 |
| 2006/0288483 | A1 * | 12/2006 | Naslund et al. | 5/601 |

OTHER PUBLICATIONS

"Neonatal Chest Wall Suspension Splint: A Novel and Noninvasive Method for Support of Lung Volume" by Thomas L. Miller, Charles Palmer, Thomas H. Shaffer, and Marla R. Wolfson, Pediatric Pulmonology, vol. 39, pp. 512-520, 2005.

* cited by examiner

THORACIC STABILIZER

FIELD OF THE INVENTION

The present invention relates to a thoracic stabilizer for limiting anterior chest wall collapse.

BACKGROUND OF THE INVENTION

While the etiology of chest wall instability varies across age-range, the need for stabilization of the anterior chest wall is applicable to both pediatric and adult populations.

With respect to the pediatric population, marked reduction in the compliance of the lung relative to the chest wall contributes to pulmonary insufficiency, particularly in the prematurely born infant. An imbalance of forces across the chest wall caused by greater recoil of the lungs inward relative to the chest wall outward, results in reduced resting lung volume. Furthermore, because the rib cage is incompletely ossified and the respiratory muscles are underdeveloped, the chest wall of the newborn is vulnerable to inward distortion during inspiration. Respiratory efforts are dissipated on distorting the chest wall rather than effectively exchanging tidal volumes. Distortion of the chest wall during inspiration is characterized by varying degrees of anterior-posterior motion at the xyphoid-sternal junction (anterior retraction), inward motion between or within the intercostals spaces (intercostals retraction), inward motion below the lower rib cage margin (subcostal retraction), and asynchronous/paradoxical motion between the chest wall and abdomen.

Surgical and ventilatory therapies have been used to mitigate anterior retraction of the chest wall for the pediatric population, in order to increase lung volume and promote effective inspiration. In neonates with respiratory distress syndrome, "xiphoid hook", continuous negative extrathoracic pressure (CNP) and continuous positive airway pressure (CPAP) have been shown to reduce anterior chest wall retraction and improve respiratory indices. However, all of these tools have limitations. The surgical approach is problematic because of tissue fragility. CNP ventilation is challenging because it typically requires complex ventilation units, tight seals, and has been associated with adverse effects (e.g., gastric and intestinal distention). CPAP delivered by way of nasal cannulae or prongs (NCPAP), which is the most common means of pressure support in spontaneously breathing neonate, improves lung volume and oxygenation and reduces chest wall distortion. NCPAP is not completely benign, however, mostly due to complications such as inconsistency in, and loss of, distending pressure with an open mouth or poor fitting nasal prongs, nasal trauma as well as gaseous distention of the abdomen. Positive end-expiratory pressure (PEEP) supports lung volume and the relatively flaccid chest wall during mechanical ventilation. High PEEP, however, may impair cardiac output, contribute to ventilation-perfusion mismatch and ventilator-induced lung injury.

With respect to the adult population, there are numerous clinical conditions causing anterior chest wall instability with pulmonary complications, such as neuromuscular and musculoskeletal disorders. Acute flail chest, for example, is one of the most common serious traumatic injuries to the thorax with morbidity linked to the acute underlying lung consequences. Flail chest is traditionally described as a paradoxical movement of a segment of chest wall caused by fractures of 3 or more ribs broken in 2 or more places, anteriorly and posteriorly, and unable to contribute to lung expansion. Acute intervention since the late 1950's includes "firm strapping" of the affected area to prevent the flail-like motion, laying the patient with the flail segment down to prevent it from moving out paradoxically during expiration, the use of towel clips placed around rib segments and placed in traction to stabilize the rib cage, intubation with positive pressure ventilation to stent the ribcage, and surgical approaches in which both ends of a fractured rib must be stabilized for operative intervention to be most effective. There is, however, a high level of long-term disability in patients sustaining flail chest characterized by a 22% disability rate with over 63% having long-term problems, including persistent chest wall pain, deformity, and dyspnea on exertion.

SUMMARY OF THE INVENTION

According to one aspect of the invention, a thoracic stabilizer for limiting anterior chest wall collapse includes a platform and a pair of lateral supports. The platform is adapted to support at least a part of a patient such that a force is applied to the platform by the patient. The lateral supports are arranged to contact opposite sides of the patient's chest wall and apply force to the chest wall to limit collapse of the anterior portion of the chest wall. The magnitude of the force applied to the chest wall by the lateral supports is varied depending on the force applied to the platform by the patient.

According to one embodiment, the thoracic stabilizer comprises a retractometer adapted to measure the collapse of the chest wall. The force applied to the chest wall by the lateral supports depends on the magnitude of the chest wall collapse as well as the force that is applied to the platform by the patient. According to one embodiment, the thoracic stabilizer comprises a controller that varies the force applied to the chest wall in closed-loop fashion based on the collapse of the chest wall measured by the retractometer.

According to one embodiment, the thoracic stabilizer comprises motors coupled to the lateral supports for moving the lateral supports with respect to the platform. According to another embodiment, the thoracic stabilizer comprises a hydraulic system and the lateral supports include expandable fluid-filled members coupled to the hydraulic system to expand to apply force to the chest wall.

According to one aspect of the invention, a thoracic stabilizer comprising a platform, left and right lateral supports, a retractometer, a controller and sensors associated with the platform and the lateral supports is provided. The platform sensor, the lateral support sensors, and the retractometer respectively generate signals representing force applied to the platform by a patient, force applied to the chest wall by the lateral supports and the magnitude of the chest wall collapse. The controller is adapted to receive the signals and set the force applied to the chest wall by the lateral supports depending on the force applied to the platform by the patient and the magnitude of the chest wall collapse using an algorithm of the controller.

DESCRIPTION OF THE INVENTION

Figure 1:
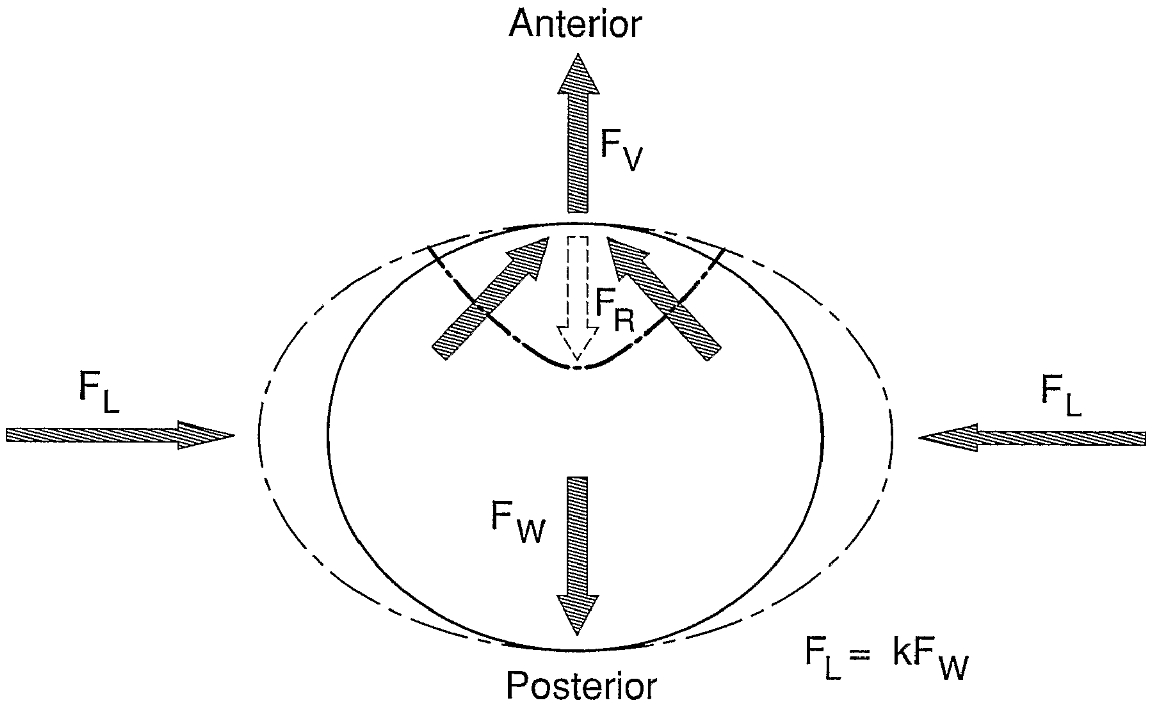
FIG. 1 is a schematic sectional illustration of a chest wall illustrating the application of forces to the lateral chest wall to limit anterior chest wall retraction according to the present invention.

Referring to the drawings, where like numerals identify like elements, the chest wall is illustrated schematically in FIG. 1 as a generally circular structure having hoop-type continuity. As described below in greater detail, the present invention provides a device that supports the patient's weight (represented by arrow $F_W$) and applies force (represented by arrows $F_L$) to opposite sides of the lateral chest wall. The application of the lateral forces $F_L$ to the patient results in application of a vertical force (represented by arrow $F_V$) to the anterior chest wall because of hoop continuity about the chest wall. The application of force, $F_V$, to the anterior chest wall counteracts retractions of the chest wall (represented by arrow $F_R$) during respiration. The present invention provides for stabilization of the thorax with an orthotic that is portable, self-adapting, simple to use, and inexpensive without requiring customized fitting or adhesives for maintaining contact with the chest wall.

There are multiple embodiments of devices each adapted to apply lateral forces to the chest wall to stabilize an anterior portion of the chest wall. The stabilizing devices may include mechanical, hydraulic, fluidic or electrical components. Certain components may be common to all embodiments. For example, lateral supports could includes pads, cushions, elastic bands, gel, visco-elastic memory foam, water-filled walls, etc. The anterior chest wall sensor (retractometer) for monitoring the severity of retractions may be mechanical, electrical, hydraulic, or pneumatic in nature. The retractometer may comprise a soft pad attached to a gear shaft/spring-loaded gear assembly. The spring-loaded gear may be adapted to transmit a mechanical or electrical signal in response to chest wall displacement. For example, as the chest wall retracts downward, the gear shaft extends downward turning the gear assembly. Another example of a retractometer comprises a gas-filled tube that is wrapped around the chest wall with a side port at the xyphoid-sternum junction to measure pressure in the tube. Alternatively, the retractometer may comprise a nozzle positioned at the xyphoid-sternum junction. As the chest wall pulls inwardly, pressure in the tube or nozzle drops. Output from the retractometer may be mechanical, pneumatic, or electrical.

As described below, each of the embodiments applies lateral force to the patient's chest wall according to an algorithm based in part on the patient's weight and in part on the magnitude of the anterior chest wall retractions as measured by a retractometer to reduce the retractions, preferably to approximately zero. Depending on the embodiment, the feedback signals from the retractometer may be mechanical, hydraulic, pneumatic or electronic in nature. The algorithm used by the thoracic stabilizer may determine $F_L$ proportionally, integratively or differentially based on the feedback signals from the retractometer.

Figure 2:
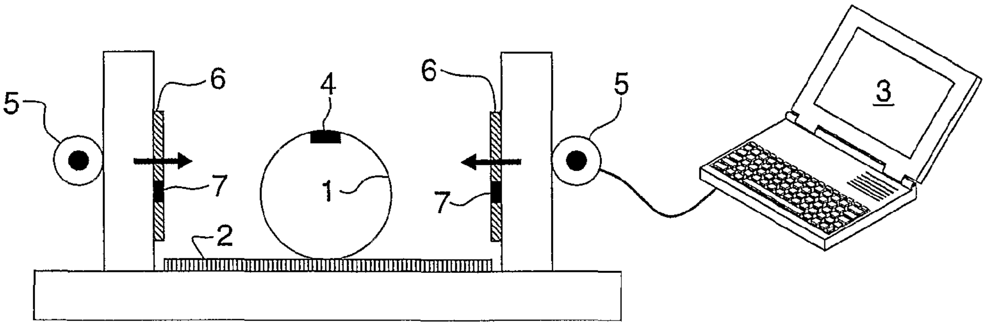
FIG. 2 is an elevation view of a thoracic stabilizer according to a first exemplary embodiment of the invention.

Referring to FIG. 2, there is shown a thoracic stabilizer according to a first exemplary embodiment of the invention. The patient, having a chest wall 1 represented schematically by a circle and a body weight $F_W$, is supported on a platform. The thoracic stabilizer includes a force transducer 2 located within the platform, a microprocessor (e.g., CPU) 3, and a retractometer 4 for measuring the magnitude of retractions of the anterior chest wall portion of the patient. The stabilizer also includes servo motors 5 that are adapted to drive lateral supports 6 inwardly with respect to the platform for application of lateral forces to the chest wall 1. In response to the body weight, $F_W$, applied by the patient, the force transducer 2 generates a signal that is transmitted to the microprocessor 3.

Figure 3:
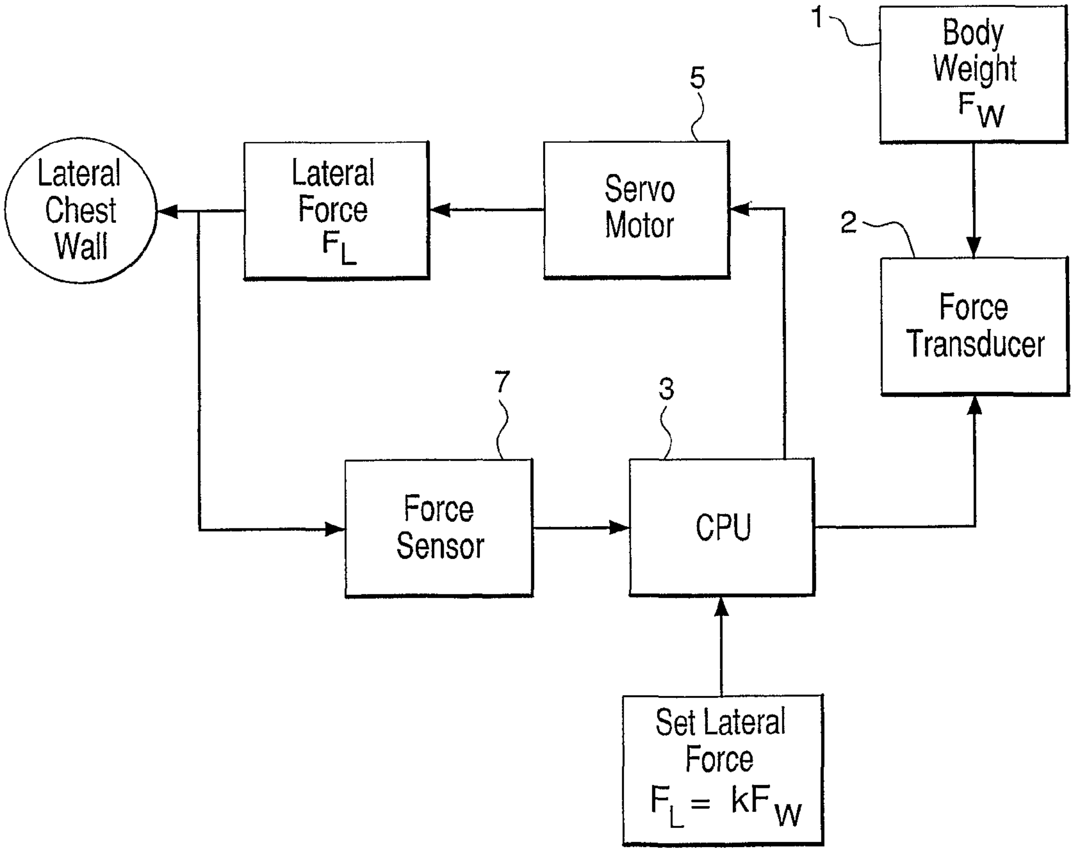
FIG. 3 is a flow diagram of the operation of the thoracic stabilizer of FIG. 2.

Referring to flow diagram of FIG. 3, the thoracic stabilizer of FIG. 2 operates as follows. The microprocessor 3 compares the information from the force transducer 2 representing patient weight and determines a set-point for the lateral force $F_L$ to be applied to the patient's chest wall according to an algorithm based in part on the patient's weight (e.g., $kF_W$) and in part on the magnitude of the chest wall retractions measured by the retractometer. The output from the microprocessor 3 drives the servo-motors 5 to move the lateral supports 6 inwardly to deliver lateral force $F_L$ to the lateral chest wall. The $F_L$ applied by the lateral supports 6 is monitored by a force sensor 7 which transmits a feedback signal back to the microprocessor 3. In response to the feedback signals from the retractometer 4 and the force sensors 7, the algorithm of the microprocessor modulates the applied force, $F_L$, in closed loop fashion to reduce the chest wall retractions measured by the retractometer 4 to approximately zero. Preferably, the algorithm used by the microprocessor 3 limits the lateral force ($F_L$) applied to each side of the chest wall such that the force applied to the patient does not exceed the forces that would be applied to the lateral chest wall by body weight were the patient to be sidelying.

Figure 4:
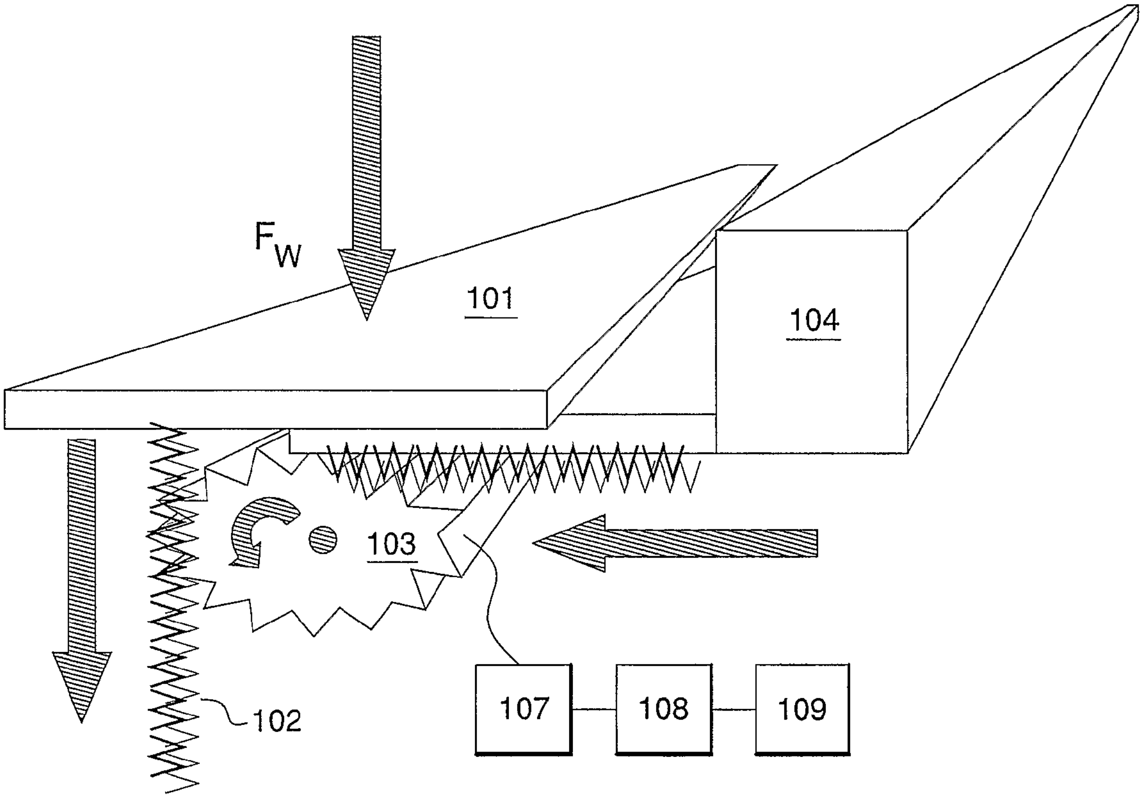
FIG. 4 is an elevation view of a thoracic stabilizer according to a second exemplary embodiment of the invention.

The embodiment shown in FIG. 2 may be referred to as electrical because electrical signals are transmitted to servo-motors to drive the lateral supports. Referring to FIG. 4, there is shown a thoracic stabilizer according to another exemplary embodiment of the invention that is mechanical in nature. In this embodiment, the downward force applied to a platform 101 of the stabilizer by the subject's weight ($F_W$) is transmitted via a vertical shaft 102 to a gear drive system 103. The gear drive system 103 rotates such that the teeth of each gear interdigitate to result in an inward movement and applied force ($F_L$) for each lateral support 104, of which only one is shown. As shown, the right lateral chest wall support is attached to the gear drive system 103, which pulls the lateral support inwardly with as a function of $F_W$ (i.e., the applied force is related to the characteristics gear system such as gear diameter, number of teeth).

The stabilizer of FIG. 4 includes a retractometer 109 to measure the magnitude of the anterior chest wall retraction. The stabilizer also includes a transmission (e.g., series of gears) 107 and microprocessor 108 coupled between the gear drive system 103 and the retractometer 109. The microprocessor 108 uses an algorithm to adjust $F_L$ (proportionally, integratively, or differentially) in relation to the subject's weight and the magnitude of the retractions via transmission 107 and gear drive system 103 in response to signals from the retractometer 109. The retractometer 109 may include a gear shaft/gear assembly, as described above. In this embodiment, the feedback signals from the retractometer are mechanical forces or displacements that are based on the movement of the gear shaft of the retractometer as retraction are reduced, preferably to approximately zero. Similar to the above-described electrical embodiment, the mechanical stabilizer is preferably adapted to limit the $F_L$ that can be applied to $F_W$ (i.e., that force which would be applied to the lateral chest wall by the subject's weight were the subject sidelying).

Figure 5:
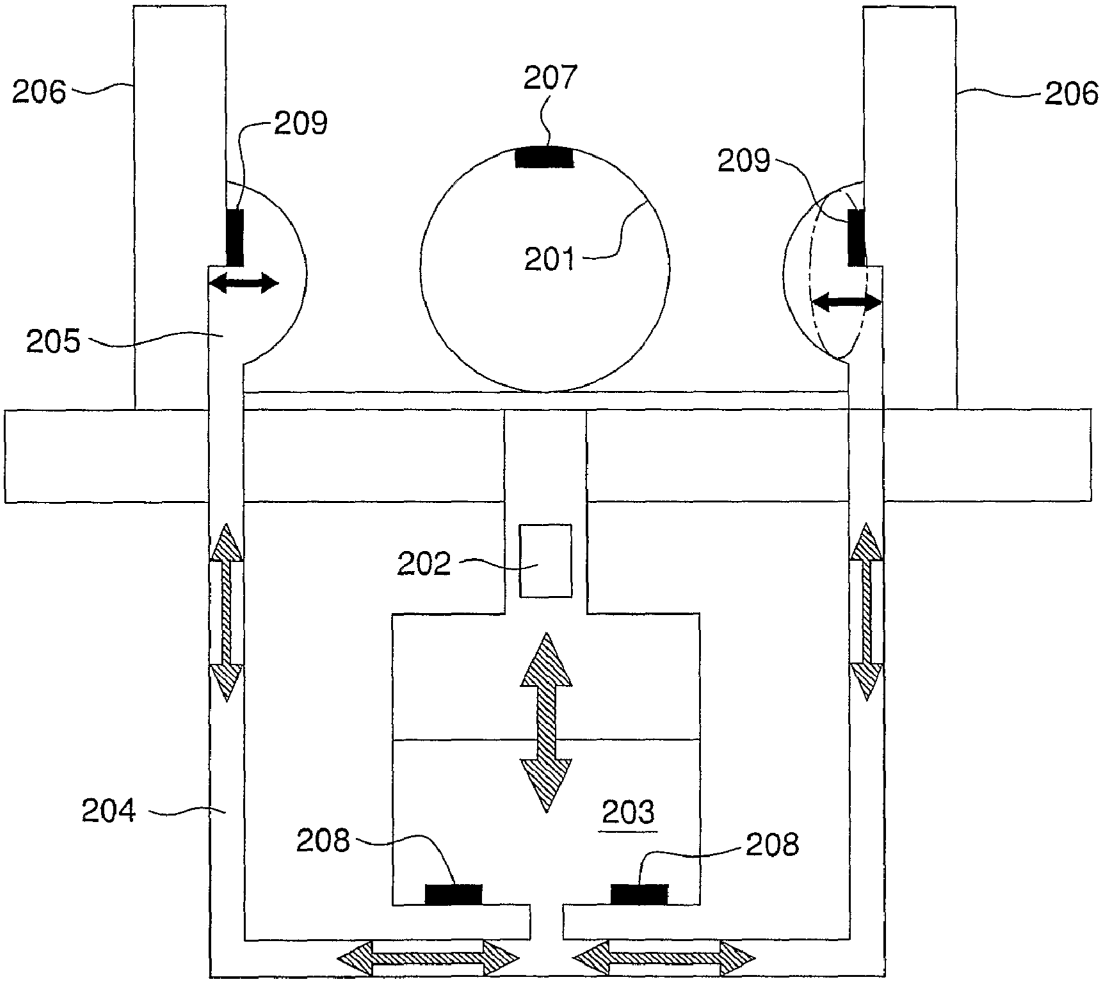
FIG. 5 is an elevation view of a thoracic stabilizer according to a third exemplary embodiment of the invention.

Referring to FIG. 5, there is shown a thoracic stabilizer according to another exemplary embodiment that is hydraulic in nature. In this embodiment, the downward force of the subject's weight ($F_W$) is transmitted via a piston 202 that is embedded within a platform. This piston compresses a fluid-filled cylinder 203 which delivers said fluid via channels 204 into elastic walled, expandable/collapsible like-fluid filled lateral supports 205. The lateral supports are attached to sliding side walls 206 which are preferably preset to contact the subject's chest wall with the lateral supports in the collapsed position. The hydraulic piston-fluid filled cylinder is configured such that the amount of fluid that is displaced exerts a lateral force to the chest wall. The amount of lateral force $F_L$ is determined in part by a retractometer 207 (e.g., chest motion sensor) which measures the magnitude of anterior chest wall retraction, and in part by the subject's weight $F_W$. Fluid sensors (208, 209) respectively located within the fluid-filled cylinder 203 and lateral supports 205 are adapted to transducer pressure within these components. The fluid sensors may transduce signals that are electronic, pneumatic or fluidic in nature. A microprocessor 210 uses an algorithm to determine (proportionally, integratively, or differentially) the applied $F_L$ based on feedback signals from the retractometer 207 and the fluid sensors 208, 209. According to one embodiment, the feedback is used to displace fluid within the system to modulate the lateral force in proportion to the subject's weight and the magnitude of the anterior chest wall retractions such that $F_L=(A_2/A_1)F_W$ and that the lateral force applied to each side cannot exceed $F_W$ thereby limiting the net force to the lateral chest wall to that experience when side-lying.

The foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A thoracic stabilizer for limiting anterior chest wall collapse comprising:

a platform adapted to support at least a part of a patient such that a force is applied to the platform by the patient;

a retractometer adapted to measure collapse of the anterior portion of the chest wall of the patient; and a pair of lateral supports arranged to contact opposite sides of the patient's chest wall to apply force to the chest wall for limiting collapse of an anterior portion of the chest wall, the force applied to the chest wall by the lateral supports being varied depending on the force applied to the platform by the patient, wherein the magnitude of the force applied to the chest wall by the lateral supports depends on the magnitude of the chest wall collapse measured by the retractometer.

2. The thoracic stabilizer according to claim 1, further comprising a controller for controlling the magnitude of the force applied to the chest wall by the lateral supports.

3. The thoracic stabilizer according to claim 2, wherein the controller varies the force applied to chest wall by the lateral supports in closed loop fashion based on the collapse of the chest wall measured by the retractometer.

4. The thoracic stabilizer according to claim 2 further comprising a force transducer coupled to the platform, the force transducer adapted to transmit a signal to the controller representing the force applied to the platform by the patient, the controller adapted to set the force applied by the lateral supports based on the signal from the force transducer and the chest wall collapse measured by the retractometer.

5. The thoracic stabilizer according to claim 4, wherein the controller includes a microprocessor and wherein the force applied to the chest wall by the lateral supports is set by the controller according to an algorithm of the microprocessor.

6. The thoracic stabilizer according to claim 2 further comprising force sensors coupled to the lateral supports for transmitting a signal to the controller representing the force applied to the chest wall by the lateral supports.

7. The thoracic stabilizer according to claim 1 further comprising motors coupled to the lateral supports for moving the lateral supports with respect to the platform.

8. The thoracic stabilizer according to claim 7 further comprising transmissions coupled between the motors and the lateral supports.

9. The thoracic stabilizer according to claim 1 further comprising a hydraulic system, the lateral supports including expandable fluid-filled members coupled to the hydraulic system and adapted to expand for applying force to the chest wall.

10. The thoracic stabilizer according to claim 9, wherein the hydraulic system includes a piston and a fluid-filled cylinder coupled between the platform and the lateral supports, the piston adapted to compress the fluid-filled cylinder in response to the force applied to the platform by the patient for expanding the expandable members of the lateral supports.

11. A thoracic stabilizer for limiting collapse of the anterior portion of a patient's chest wall, the thoracic stabilizer comprising:

a platform adapted to support at least a part of a patient such that a force is applied to the platform by the patient;

a sensor associated with the platform and adapted to generate a signal representing the force applied to the platform by the patient;

left and right lateral supports arranged for contact with left and right sides of the patient's chest wall to apply force to the chest wall for limiting collapse of an anterior portion of the chest wall;

sensors associated with the left and right lateral supports and adapted to generate signals representing the forces applied to the chest wall by the lateral supports;

a retractometer adapted to measure collapse of the anterior portion of the chest wall of the patient, the retractometer generating a signal representing the collapse of the chest wall; and a controller for controlling the force applied to the chest wall by the lateral supports, the controller operably connected to the lateral support sensors, the platform sensor and the retractometer for receiving the respective signals, the controller adapted to set the force applied to the chest wall by the lateral supports depending upon the force applied to the platform by the patient and the magnitude of the chest wall collapse using an algorithm of the controller.

12. The thoracic stabilizer according to claim 11, wherein the controller is adapted to vary the force that is applied to the chest wall by the lateral supports in closed-loop fashion based on changes in the magnitude of the chest wall collapse measured by the retractometer to substantially eliminate the chest wall collapse.

13. The thoracic stabilizer according to claim 11 further comprising motors operably coupled to the lateral supports for moving the lateral supports with respect to the platform.

14. The thoracic stabilizer according to claim 11 further comprising a hydraulic system, the lateral supports including expandable fluid-filled members coupled to the hydraulic system and adapted to expand for applying force to the chest wall.

15. A method of treating anterior chest wall collapse of a patient comprising the steps of:

providing a thoracic stabilizer including a platform for supporting at least a portion of a patient such that the patient applies a force to the platform, the platform including a force transducer for generating a signal representing the force applied to the platform by the patient, the thoracic stabilizer including a pair of lateral supports adapted to contact opposite lateral sides of the chest wall of the patient and apply force to the chest wall;

providing a retractometer adapted to measure collapse of an anterior portion of the chest wall of the patient;

providing a controller adapted to control the lateral supports for setting the force applied to the chest wall by the lateral supports, the controller including an algorithm for determining force to apply to the chest wall using the lateral supports based on the force applied to the platform by the patient and the magnitude of the chest wall collapse;

positioning a patient such that a portion of the patient is supported by the platform;

measuring the magnitude of the collapse of the chest wall of the patient using the retractometer;

measuring the magnitude of the force applied to the platform by the patient using the force transducer;

setting the force applied to the chest wall by the lateral supports using the algorithm of the controller;

measuring a reduced collapse of the chest wall using the retractometer;

adjusting the force applied to the chest wall based on the reduced collapse using the algorithm of the controller; and repeating the steps of measuring a reduced collapse and adjusting the force applied to the chest wall in a closed-loop manner to substantially eliminate collapse of the chest wall.

16. A thoracic stabilizer for limiting anterior chest wall collapse comprising:

a platform adapted to support at least a part of a patient such that a force is applied to the platform by the patient;

a pair of lateral supports arranged to contact opposite sides of the patient's chest wall to apply force to the chest wall for limiting collapse of an anterior portion of the chest wall, the force applied to the chest wall by the lateral supports being varied depending on the force applied to the platform by the patient; and motors coupled to the lateral supports for moving the lateral supports with respect to the platform.

* * * * *